United States Patent [19]
Hoffman et al.

[11] Patent Number: 5,620,875
[45] Date of Patent: Apr. 15, 1997

[54] TRANSFER OF TAXOL FROM YEW TREE CUTTINGS INTO A CULTURE MEDIUM OVER TIME

[75] Inventors: Angela Hoffman, Beaverton; Courtney C. J. Voelker; Alyssa T. Franzen, both of Portland, all of Oreg.

[73] Assignee: University of Portland, Portland, Oreg.

[21] Appl. No.: 390,125

[22] Filed: Feb. 17, 1995

[51] Int. Cl.$^6$ .............................. C12P 17/02; C12P 1/00
[52] U.S. Cl. ........................... 435/123; 435/41; 435/420; 549/510
[58] Field of Search ............................... 435/123, 240.1, 435/41, 240.46, 240.48; 549/510

[56] References Cited

PUBLICATIONS

Arbuck, Susan G. et al., Clinical Development of Taxol, 1993a, *Journal of the National Cancer Institute Monographs*, 15:11–24.
Arbuck, Susan G. et al., A Reassessment of Cardiac Toxicity Associated with Taxol, *Journal of the National Cancer Institute Monographs*, 15:117–130, 1993.
Coughlan, A., Yew tree yields anticancer culture, *New Scientist*, 9 Jan. 1993, p. 21.
Fett–Neto and DiCosmo, Distribution and Amounts of Taxol in Different Shoot Parts of *Taxus cuspidata*, *Planta Med.* 58:464–466, 1992.
Guenard, D., et al., Taxol and Taxotere: Discovery, Chemistry, and Structure–Activity Relationships, *Acc. Chem. Res.*, 1993, 26, 160–67.
Hei and Hall, Taxol, Radiation, and Oncogenic Transformation, *Cancer Research* 53:1368–72, Mar. 15, 1993.
Hoffman and Franzen, Taxane Production by Yew Tree Cuttings, *Proceedings of the Oregon Academy of Science*, vol. XXX, 20:22.
Joyce, C., Taxol: search for a cancer drug, *BioScience* 43 (3):133–36 (1993).
Millipore Waters Chromatography, 1993–94. *The Waters Chromatography Handbook*, Milford, Massachusetts; Millipore Corporation. P. 20–22, 30–31.
Richeimer, et al., High–Performance Liquid Chromatographic Assay of Taxol, *Anal. Chem.*, 64:2323–36, 1995.
Sigma Chemical Company Catalog, 1991–92; *Plant Cell Culture*, St. Louis, p. 53.
Taxol Gains Quick FDA Approval, *Science* 259:181 (8 Jan. 1993).
U.S. Department of Health and Human Services, 1990, *NCI Investigational Drugs: Pharmaceutical Data*, 151–53.
Witherup et al., High Performance Liquid Chromatographic Separation of Taxol and Related Compounds From *Taxus brevifolia*, *Journal of Liquid Chromatoraphy* 12:11, 2117–2132 (1989).
Wickremesinhe et al, J of Liquid Chromatography, vol. 16, pp. 3263–3274(1993).
Strobel, et al., Plant Science, vol. 84, pp. 65–74, 1992.

*Primary Examiner*—Irene Marx
*Attorney, Agent, or Firm*—Klarquist Sparkman Campbell Leigh & Whinston, LLP

[57] ABSTRACT

Taxol, an antineoplastic drug, has shown cytotoxic activity against numerous malignant tumors including: breast cancer, colon cancer, ovarian cancer, and skin cancer. Taxol is found in many species of yew including: slow-growing *Taxus brevifolia* and faster-growing *Taxus media X Hicksii*. Yew tree cuttings were cultured and the medium was extracted weekly, bi-weekly, and tri-weekly over a period of nine weeks. Taxol and other taxanes were separated through a multi-step procedure using hexane extractions, C-18 Sep Pak cartridges, and high performance liquid chromatography (HPLC). The concentration of the taxanes was then calculated. Taxol and other taxanes can continue to be transferred into a culture medium and extracted over a nine-week period. There is a higher yield when extracted weekly.

10 Claims, 3 Drawing Sheets

TAXOL

10-DEACETYL TAXOL

CEPHALOMANNINE

7-EPI-10-DEACETYL TAXOL

TAXOL

TRANSFER OF TAXOL FROM YEW TREE CUTTINGS INTO A CULTURE MEDIUM OVER TIME

BACKGROUND OF THE INVENTION

Cancer is one of the leading causes of death in our country today. Despite extensive research, a cure for cancer is not yet a reality. Taxol is known to be cytotoxic against numerous malignant tumors. The results of studies indicate that taxol has been effective against breast cancer, colon cancer, skin cancer, carcinosarcoma in rats, leukemia in mice, malignant melanoma, and ovarian cancer (Hei and Hall 1993; Joyce 1993; Coghlan 1993; Guenard, Gueritte-Voegelein, and Pitier 1993).

After thirty years of research, taxol is no longer an experimental drug. In December, 1992, the Food and Drug Administration (FDA) approved taxol, also known as Paclitaxal, for general use in patients with advanced ovarian and breast cancer.

Studies show taxol to be an inhibitor of cell division. The cellular target of taxol is tubulin. Other cancer drugs prevent the assembly of tubulin into microtubules, but taxol promotes tubulin assembly and inhibits the disassembly process (Guenard, Gueritte-Voegeiein, and Pitier 1993; Richeimer, Tinnermeier, and Timmons 1992; Coghlan 1993). Taxol blocks cells at the $G_2$ and M phases of the cell cycle (Hei and Hall 1993).

Taxol was discovered in 1963 in the bark of the Pacific yew (*Taxus brevifolia*), a slow-growing environmentally sensitive native tree often found in the old-growth forests (Joyce 1993; "Taxol " 1993). Taxol and similar compounds are also found in other species of yew.

If taxol therapy is approved for other types of cancer, the current taxol supply will be rapidly depleted. Each treatment requires 300 milligrams of taxol and four to ten doses are required for a total regimen. The result is an average of two grams of taxol per cancer patient. If 12,000 cancer patients are treated, 24 kilograms of taxol would be needed. It takes 30 pounds of bark to produce one gram of taxol; therefore, 60 pounds of bark are needed per cancer patient. On an average, 12.5 pounds of bark are produced per yew tree (Joyce 1993).

The separation of taxol is very difficult and requires a multi-step procedure. Yew trees produce other chemicals called taxanes that are similar in structure to taxol. FIG. 1 shows the chemical structure of taxol (Arbuck, 1993a). Structural differences between taxol and various taxanes are as follows: for baccatin, the group at C 13 is replaced with -OH; for 10-deacetyl baccatin III, the group at C 13 is replaced with -OH, and -OAc at C 10 is replaced with -OH); for cephalomannine, the two starred C's are removed to make a butyl group; for 10-deacetyl taxol, the -OAc at C 10 is replaced with -OH, and the -OH at C 7 switches from the front to the back of the structure.

The baccatin group is the most similar in structure to taxol, but without the side chain on carbon 13. Total synthesis has taken years to develop due to the complex molecular structure of taxol. Final synthesis of taxol was published in February, 1994. A semi-synthetic taxol product, Taxotere, can be made from 10-deacetyl baccatin III.

Because of the enormous demand for taxol and the limited natural supply of yew trees, scientists and researchers are trying to develop new and effective ways of producing the drug. Scientists have extracted taxol and other taxanes from yew needles, bark, tree fungus, and other species besides *T. brevifolia*. One of these studies found that cuttings of certain *Taxus* species transfer taxol into the culture medium (Hoffman and Franzen 1994). The purpose of this study was to determine whether taxol could be transferred from yew tree cuttings into a culture medium over time.

SUMMARY OF THE INVENTION

Taxol, a cancer-fighting chemical, is found in the slow-growing yew tree often located in old-growth forests. Taxol is in high demand and new ways of producing the chemical are essential. Our experiment found that yew cuttings can transfer taxol into a culture medium over time. The most productive method is to extract the medium weekly. This method could be used to mass produce taxol.

EXPERIMENTAL PROCEDURE

Figure 1:
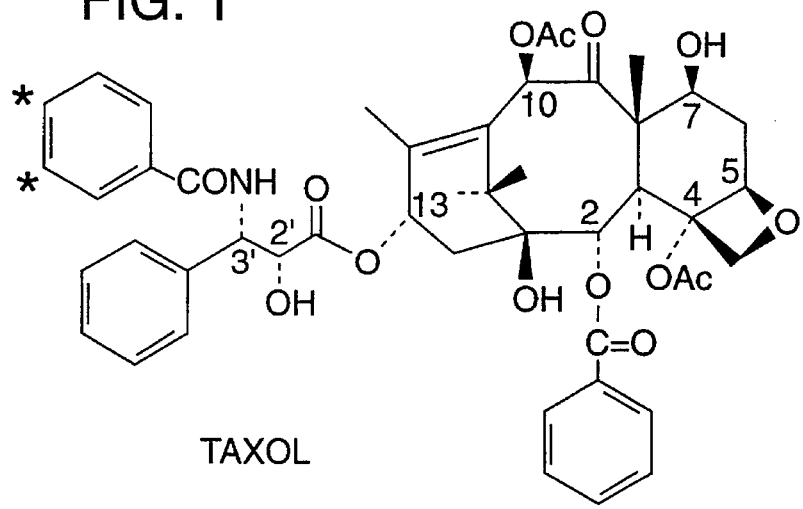
FIG. 1 shows the chemical structure of taxol. The two starred carbons are removed to make a butyl group in cephalomannine.

Yew tree cuttings were donated from the Carlson Tree Farm near Troutdale, Oreg. The species of yew tree used in this experiment was *T. media X Hicksii*, which is a hybrid between *T. brevifolia* and *T. cuspidata*.

Yew cuttings were thoroughly scrubbed with a toothbrush, soap, and water, soaked for 2 minutes in a 70% ethanol solution, and for 2 minutes in a 20% bleach (Clorox) solution. The soaking process was repeated 4 times and the cuttings were rinsed in sterile distilled water.

Using standard sterile techniques, 5 ml of Gambourg's B-5 liquid culture medium (Sigma), supplemented with 3% sucrose and $5 \times 10^{-6}$ M 2,4-dichlorophenoxyacetic acid and one washed cutting were placed into each vial. Sterile cotton was placed in the opening. The cuttings were incubated at low light in a Lab-Line Biotronette Plant Growth Chamber (temperature, 18° C. from 6 am to 10 pm and 12° C. from 10 pm to 6 am). Triplicate sets of samples were divided into 3 groups of 9 vials each. The medium in each group was extracted and replaced at a specified time: after 1 week for group 1, after 2 weeks for group 2, and after 3 weeks for group 3.

In the transfer hood, a measured volume of the culture medium was removed and replaced with an equivalent volume of fresh medium. The removed culture medium was mixed with hexane in a separatory funnel and left to settle in order to remove the very nonpolar molecules. The hexane layer was discarded and small traces of hexane remaining in the aqueous layer were evaporated using a hair dryer. The aqueous layer was pushed through a C-18 Sep Pak (Millipore) which absorbed the taxol, along with similar molecules. The aqueous effluent was discarded. The taxol and other taxanes were then flushed from the Sep Pak with methanol, which was subsequently removed in a rotary evaporator (Büchi Rotovapor RE III, water bath 461 at 35° C.).

Figure 2:
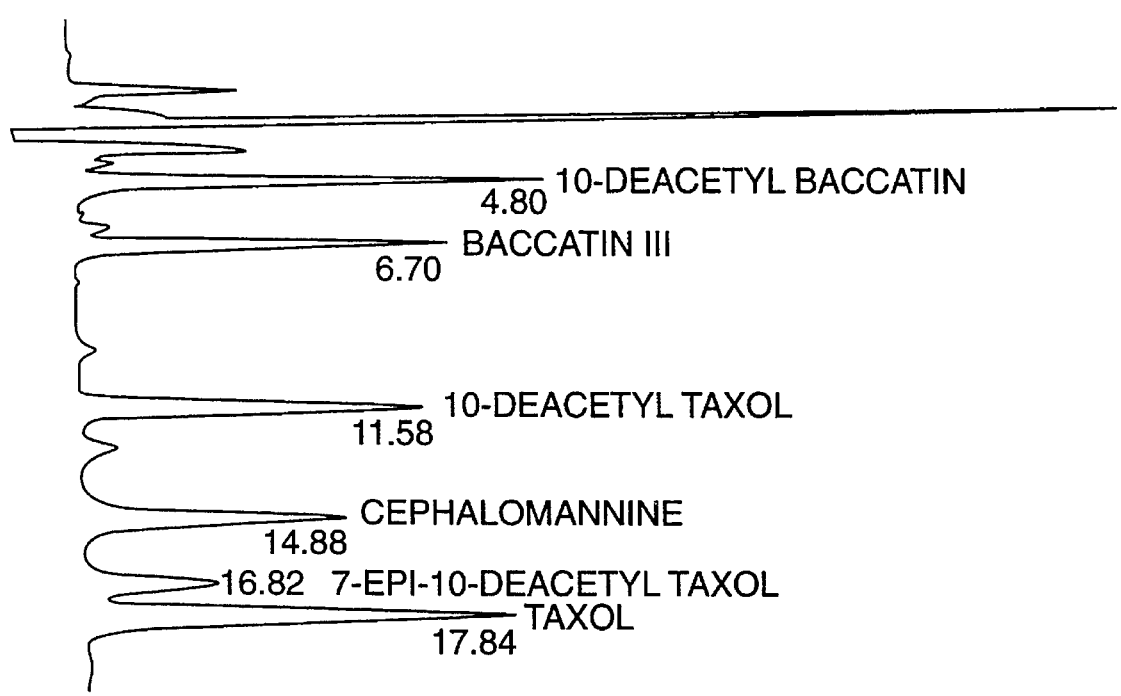
FIG. 2 shows in graphic form the separation of taxanes using the HPLC.
Figure 3A:
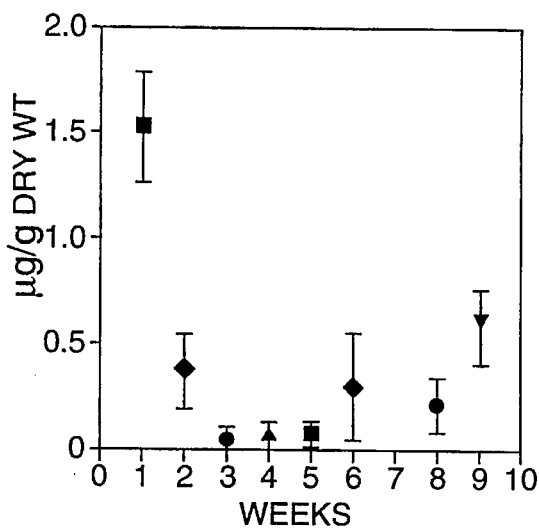
FIGS. 3A–D show weekly extractions of (A) 10-deacetyl taxol, (B) cephalomannine, (C) 7-epi-10 deacetyl taxol, and (D) taxol. The bars represent the standard error of the mean.
Figure 3B:
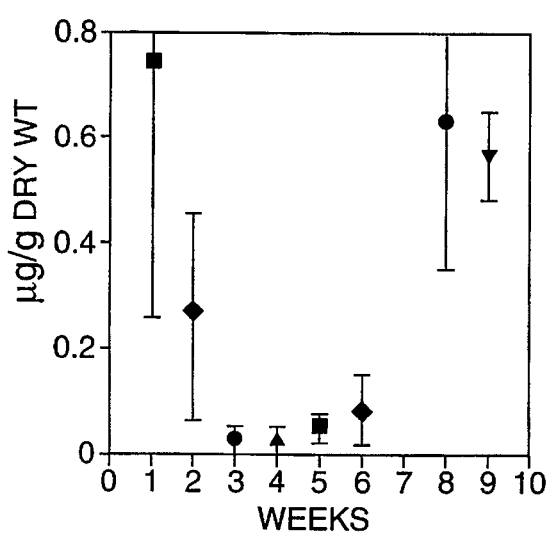
Figure 3C:
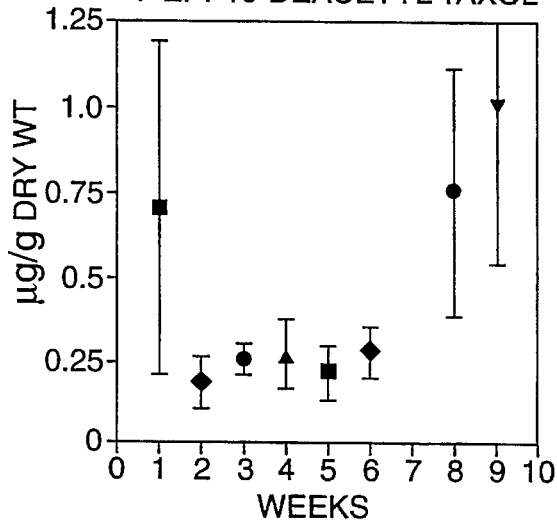
Figure 3D:
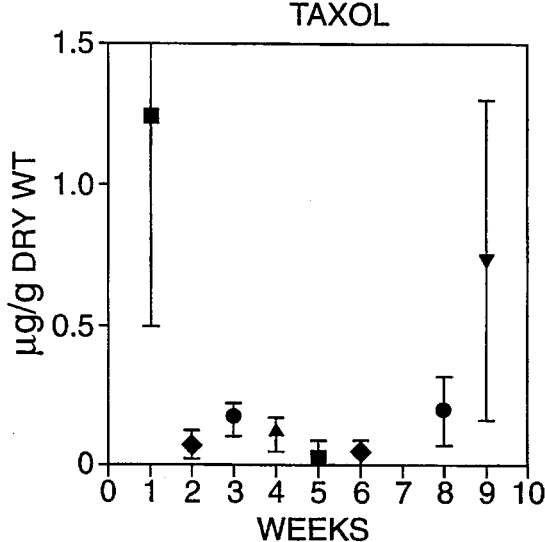

The residue from the rotary evaporation was dissolved in a known volume of methanol, filtered using a 0.2 micron filter (Millipore), injected onto the HPLC, and carried through the column by (45% A) acetonitrile and (55% B) acetate buffer. Ammonium acetate buffer pH 4.0 was made by: diluting 0.7708 g ammonium acetate and 0.6 ml acetic acid in a 1 L flask. 166 ml of ammonium acetate and 834 ml of acetic acid were added to a flask. FIG. 2 shows that the taxane standards, donated by the National Cancer Institute, are completely separated by the HPLC method used. Each taxane eluted from the column at a specified time. The instrument integrated the peak area and reported the time for each peak. The earlier the peak was removed from the column, the more polar the taxane in comparison to its molecular weight. Thus, 10-deacetyl baccatin III and baccatin III were much more polar than the taxol derivatives. See FIG. 2.

Table 1 shows the peak area for each substance that eluted from the column. The peak areas of the taxanes tested were compared with those of the pure substances. The HPLC system included: a Beckman integrator 427, Curosil B 5 micron 250×3.20 mm Phenomenex column, Beckman 110 B solvent pump, and 163 variable wavelength detector set at 228 nm.

TABLE 1

The peak areas of the taxane standards

| FILE 1. PERK# | METHOD 0. AREA % | RUN 14 RT | AREA | INDEX 14 BC |
|---|---|---|---|---|
| 1 | 6.001 | 2.02 | 121915 | 02 |
| 2 | 6.662 | 2.84 | 135329 | 02 |
| 3 | 24.025 | 3.15 | 488067 | 03 |
| 4 | 3.845 | 3.74 | 78116 | 02 |
| 5 | 6.085 | 3.87 | 123617 | 03 |
| 6 | 0.22 | 4.3 | 4472 | 01 |
| 7 | 7.581 | 4.8 | 154015 | 01 |
| 8 | 0.796 | 6.24 | 16174 | 02 |
| 9 | 7.445 | 6.7 | 151237 | 03 |
| 10 | 0.407 | 9.82 | 8277 | 01 |
| 11 | 8.478 | 11.58 | 172240 | 01 |
| 12 | 1.013 | 12.76 | 20573 | 01 |
| 13 | 8.112 | 14.88 | 164787 | 01 |
| 14 | 4.56 | 16.83 | 92646 | 02 |
| 15 | 14.769 | 17.84 | 300037 | 03 |
| TOTAL | 100. | | 203150 | |

By using the values of the peak areas, the amount of each taxane was calculated using standard curve equations (Table 2).

TABLE 2

Standard curve equations used in calculating the amounts of taxanes found in the culture medium.

| Taxane | Slope(m) | y-intercept (b) |
|---|---|---|
| 10-deacetyl baccatin III | 18216667.3 | 1407.9 |
| baccatin | 7981048.5 | 246.9 |
| 10-deacetyl taxol | 819431.5 | 185.8 |
| cephalomannine | 416044.7 | 2044.7 |
| 7-epi-deaceytl taxol | 984318.1 | 783.3 |
| taxol | 1225958.3 | −63.3 |

$y = mx + b$
$y$ = the peak area of the HPLC graph

RESULTS

The amounts of the taxanes separated were measured over a period of nine weeks. A total of 43 samples were extracted weekly, 22 bi-weekly, and 16 tri-weekly. The amounts were calculated in micrograms per gram dry weight based on the amount of plant material in the vial. The values in Table 3 represent the averages for each taxane over the specified time period. All six taxanes were found in the medium over the nine-week test period. More taxol, cephalomannine, and 7-epi-10 deacetyl taxol were recovered from the samples that were extracted weekly than from those extracted bi-weekly or tri-weekly. There was little or no change in the recovered amounts of 10-deacetyl baccatin III, baccatin III, and 10-deacetyl taxol when compared weekly, bi-weekly, and tri-weekly (Table 3).

TABLE 3

Summary of the weekly, bi-weekly, and tri-weekly extractions of the six taxanes tested.

| TAXANES | 10DBIII | BIII | 10DT | C | 7EDT | T |
|---|---|---|---|---|---|---|
| | WEEKLY EXTRACTIONS n = 43 | | | | | |
| AVERAGE* | 0.153 | 0.199 | 0.336 | 0.393 | 0.453 | 0.276 |
| ST. ERROR | 0.018 | 0.025 | 0.729 | 0.175 | 0.091 | 0.103 |
| | BI-WEEKLY EXTRACTIONS n = 22 | | | | | |
| AVERAGE* | 0.142 | 0.205 | 0.221 | 0.074 | 0.203 | 0.067 |
| ST. ERROR | 0.031 | 0.032 | 0.113 | 0.021 | 0.028 | 0.042 |
| | TRI-WEEKLY EXTRACTIONS n = 16 | | | | | |
| AVERAGE* | 0.234 | 0.177 | 0.307 | 0.104 | 0.218 | 0.094 |
| ST. ERROR | 0.083 | 0.059 | 0.121 | 0.047 | 0.052 | 0.052 |

Figure 4A:
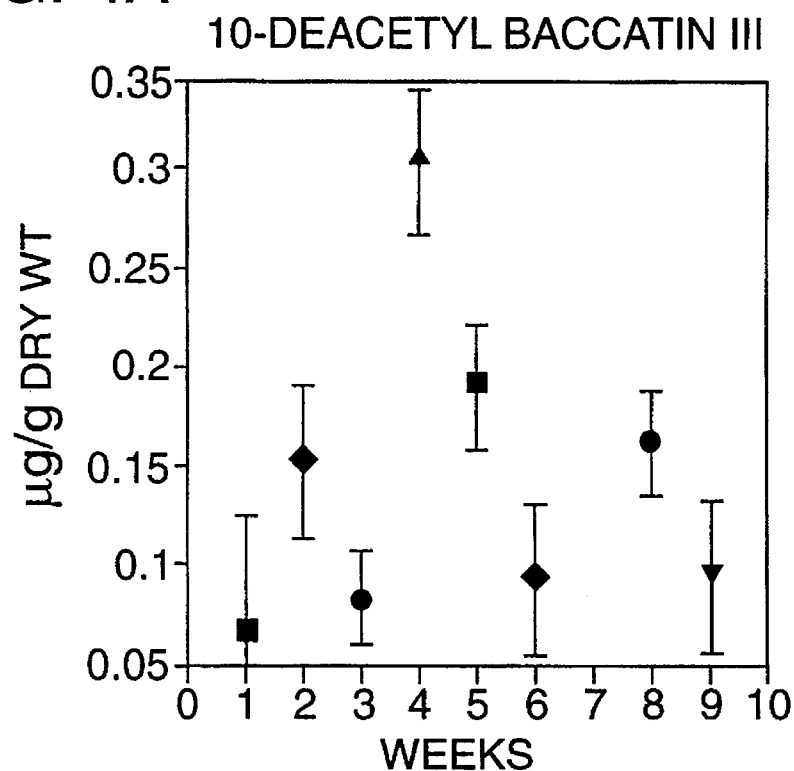
FIGS. 4A–B shows weekly extractions of (A) 10-deacetyl baccatin III and (B) baccatin III. The bars represent the standard error of the mean.
Figure 4B:
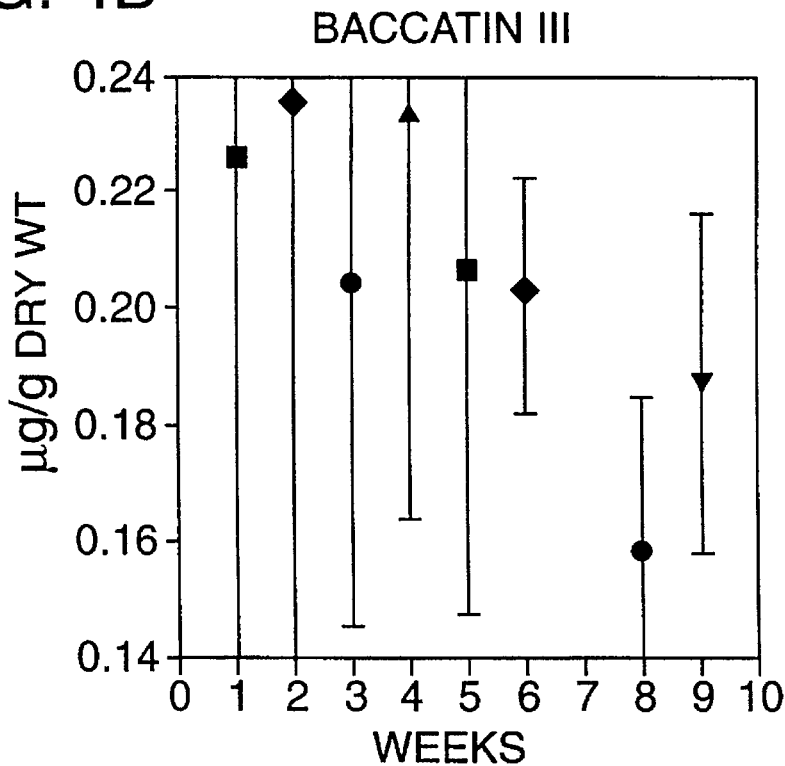

10DBIII = 10-deacetyl baccatin III
BIII = baccatin III
10DT = 10-deacetyl taxol
C = cephalomannine
7EDT = 7-epi-10 deacetyl taxol
T = taxol
ST. ERROR = standard error of the mean
*averages are in μg/g dry weight
n = the number of samples in the group FIGS. 3 and 4 present the data for weekly extractions in graphic form. In FIG. 3, cephalomannine, 10-deacetyl taxol, 7-epi-10 deacetyl taxol, and taxol have a similar pattern. Each has a higher level at the first-week extraction followed by amounts decreasing in subsequent weeks, but increasing again by the ninth week. The standard error bars indicate that there is a high level of variation in the results. It is not known if the amounts will continue to increase, plateau, or follow a fluctuating cycle after the nine weeks.

The two baccatins tested, 10-deacetyl baccatin III and baccatin III (FIG. 4), do not follow the same pattern. They have more variation than the other taxanes and lower amounts of the compounds were extracted overall.

DISCUSSION AND CONCLUSION

Yew tree cuttings continue to transfer taxol and the other five taxanes into a culture medium over a nine-week period. By extracting taxol, cephalomannine, and 7-epi-10 deacetyl taxol every week, a small but measurably greater amount of each compound was recovered, suggesting that it is beneficial to extract the medium weekly to obtain a higher yield of these three taxanes. Smaller amounts of the taxanes were extracted from the medium after two to three weeks in the culture. A possible explanation for the fact that cephalomannine, 7-epi-10 deacetyl taxol, and taxol have a higher yield when extracted weekly may be a result of the taxanes degrading over time after being transferred into the culture medium.

FIGS. 3 and 4 show two different trends in amounts of taxanes extracted weekly from the medium. In FIG. 3, it is not known if the pattern of recovery will continue after the nine weeks. The difference in recovery may be affected by many different parameters. The taxols have an ester linkage at carbon 13 whereas this group is replaced with a hydroxyl in the baccatins. The method used by the plant to make the taxanes may result in a greater production of taxol derivatives relative to the baccatins. The plant may derive the taxol-like molecules from the baccatin structure, or vice versa. The experimental method used could have favored the recovery of the taxol derivatives. The more polar baccatins may have been excluded from the C-18 Sep Pak along with the more polar substances. This would have led to more variability and lower yields of these taxanes.

In our experiment, 0.276 µg/g dry weight of taxol were extracted from the culture medium by weekly extractions. This was the total amount recovered over nine weeks. With variation, this would give between $1.73 \times 10^{-2}$ and $4.79 \times 10^{-2}$ µg/kg dry weight of plant material. Similar studies have found the bark of T. brevifolia to yield 0.01% dry weight (Arbuck 1993 b.; Witherup 1989) and T. cuspidata to yield $0.035 \pm 0.006\%$ dry weight (Fett Neto 1992). Since the numbers taken from previous studies were not obtained by special columns made to separate taxanes, 7-epi-10 deacetyl taxol and taxol were probably not separated. When the data from the present experiment was recalculated, taking this into account, $7.28 \times 10^{-5}\%$ was obtained.

Our experiment showed that taxol can be obtained by collecting the culture medium over time. The most productive method is to collect the medium weekly.

Our study used yew tree cuttings that were obtained in the winter. The time of year may have an effect on the amount of taxol transferred. Growth conditions such as temperature, light, and medium ingredients may also have an effect on the amount of taxol produced by the cuttings.

Other extractions from yew and other tree cuttings could well be achieved by the method of this invention.

Taxol is used herein to refer to the drug that now has the generic name paclitaxel and the registered trade name Taxol® (Bristol-Myers Squib Company, New York N.Y.).

REFERENCES

Arbuck, Susan G., Michaele C. Christian, Jason S. Fisherman, Corraine A. Cazenave, Gisele Sarosy, Mathew Suffness, Jonathan Adams, Renzo Canetta, Katharine E. Cole, and Michael A. 1993 a. Clinical development of taxol. *Journal of the National Cancer Institute Monographs.* 15: 11–24.

Arbuck, Susan G., H. Strauss, E. Rowinsky, M. Christian, Mr. Suffness, J. Adams, M. Oakes, M. McGuire, E. Reed, H. Gibbs, R. A. Greenfield, and M. Montello 1993 b. A reassessment of cardiac toxicology with taxol. *Journal of the National Cancer Institute Monographs.* 15: 117–129.

Coghlan, A. 1993. Yew tree yields anti-cancer culture. *New Scientist* (9 January): 21.

Fett-Neto, A. G., and F. DiCosmo. Distribution and amounts of taxol in different shoot parts of *Taxus cuspidata*. *Planta Medica.* 58:464–466 (1992).

Guenard, D. F. Gueritte-Voegelein, and P. Potier. 1993. Taxol and taxotere: discovery, chemistry, and structure-active relationships. *Accounts of Chemical Research* 26 (4): 160–7.

Hei, T. K., and E. J. Hall. 1993. Taxol radiation, and oncogenic transformation. *Cancer Research* 53 (March): 1368–72.

Hoffman, A. and A. Franzen. 1994. Taxane production in yew tree cuttings. *Proceedings of the Oregon Academy of Science* 20:22.

Joyce, C. 1993. Taxol: search for a cancer drug. *BioScience* 43 (3): 133–36.

Millipore Waters Chromatography. 1993–1994. *The Waters Chromatography Handbook.* Milford, Mass.: Millipore Corporation.

Richeimer, S. L., D. M. Tinnermeier, and D. W. Timmons. 1992. High-performance chromatographic assay of taxol. *Analytical Chemistry* 64: 2323–36.

Sigma Chemical Company. Catalog. 1991–1992. *Plant Cell Culture.* St. Louis: Sigma Chemical Company: 53.

Taxol gains quick FDA approval. 1993. *Science* 259 (8 January ): 181.

US Department of Health and Human Services. 1990. *NCI Investigational Drugs: Pharmaceutical Data.* 151–3.

Witherup, Keith M., Sally A. Look, Michael W. Stasko, Thomas G. McCloud, Haleem J. Issaq, and Gary M. Muschur. 1989. High-performance liquid chromatographic separation of taxol and related compounds from *Taxus brevifolia*. *Journal of Liquid Chromatography* 12 (November): 28.

We claim:

1. A method of obtaining a taxane from a cutting of a *Taxus* species, the method comprising the steps of:
   (a) incubating a cutting from a *Taxus* species for from one to nine weeks in an aqueous plant culture medium comprising a plant nutrient under conditions sufficient for the cutting to transfer a taxane to the medium;
   (b) removing at least a portion of the medium without removing the cutting;
   (c) recovering the taxane from the medium removed in step (b);
   (d) replacing the medium removed in step (b) with an equivalent volume of said plant culture medium; and after further incubating said cutting in the medium under conditions sufficient for the cutting to transfer additional taxane to the medium.
   (e) repeating steps (b)–(c).

2. The method of claim 1 wherein the taxane is selected from the group consisting of taxol, 10-deacetyl baccatin III, baccatin, 10-deacetyl taxol, cephalomannine, and 7 -epi -deacetyl taxol.

3. The method of claim 2 wherein the taxane is taxol.

4. The method of claim 1 wherein the *Taxus* species is selected from the group consisting of *Taxus brevifolia*, *Taxus cuspidata*, and *Taxus media x Hicksii*.

5. The method of claim 1 wherein the medium is a supplemented Gamborg's B-5 medium.

6. The method of claim 5 wherein the B-5 medium is supplemented with sucrose and 2,4-dichlorophenoxyacetic acid.

7. The method of claim 1 wherein the step of recovering the taxane comprises performing high performance liquid chromatography.

8. The method of claim 1 wherein the cutting is from a stem of the *Taxus* species.

9. The method of claim 1 wherein the *Taxus* species is selected from the group consisting of *Taxus brevifolia*, *Taxus cuspidata*, *Taxus baccata*, and *Taxus media x Hicksii*.

10. The method of claim 1 wherein medium is removed in step (b) no more frequently than about once a week.

* * * * *